(12) United States Patent
Sitnitsky et al.

(10) Patent No.: US 12,018,688 B2
(45) Date of Patent: Jun. 25, 2024

(54) SEALING ASSEMBLY FOR A PROGRESSIVE CAVITY PUMP

(71) Applicant: JOHNSON & JOHNSON SURGICAL VISION, INC., Irvine, CA (US)

(72) Inventors: Ilya Sitnitsky, Nahariya (IL); Alexander Shechtman, Haifa (IL); Assaf Govari, Haifa (IL); Stanislav Katzir, Hadera (IL); Elad Avraham Diukman, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 0 days.

(21) Appl. No.: 18/094,427

(22) Filed: Jan. 9, 2023

(65) Prior Publication Data

US 2023/0258177 A1 Aug. 17, 2023

Related U.S. Application Data

(60) Provisional application No. 63/309,779, filed on Feb. 14, 2022.

(51) Int. Cl.
| | | |
|---|---|---|
| *F01C 1/10* | (2006.01) | |
| *F03C 2/00* | (2006.01) | |
| *F03C 4/00* | (2006.01) | |
| *F04C 2/00* | (2006.01) | |
| *F04C 2/107* | (2006.01) | |

(Continued)

(52) U.S. Cl.
CPC ........ *F04C 2/1075* (2013.01); *F04C 15/0019* (2013.01); *F04C 11/001* (2013.01); *F04C 11/008* (2013.01); *F04C 2270/12* (2013.01)

(58) Field of Classification Search
CPC .. F04C 2/1075; F04C 2/1071; F04C 15/0019; F04C 15/0038; F04C 15/0049; F04C 11/001; F04C 23/001; F04C 23/008; F04C 2270/12; F01C 11/001; F16J 15/36;
(Continued)

(56) References Cited

U.S. PATENT DOCUMENTS 1,797,735 A * 3/1931 Spreen ..................... F16J 15/36
277/385
2,525,366 A * 10/1950 Meyer .................. F16J 15/3452
277/385

(Continued)

FOREIGN PATENT DOCUMENTS

| CN | 106999881 A | 8/2017 |
|---|---|---|
| EP | 641937 A1 | 3/1995 |

(Continued)

*Primary Examiner* — Theresa Trieu
(74) *Attorney, Agent, or Firm* — Johnson & Johnson Surgical Vision, Inc.

(57) ABSTRACT

A sealing assembly for a progressive cavity pump and a progressive cavity pump assembly having a retaining sleeve, a ring, and an elastic diaphragm terminating in a first end of the diaphragm in a first opening, and in a second end of the diaphragm, opposite the first end, in a second opening larger than the first opening. The second opening is held in contact with the retaining sleeve by the ring, and the first opening is configured to grip a rotor of the progressive cavity pump, and the ring is configured to hold the second opening fixed with respect to a stator of the progressive cavity pump.

16 Claims, 3 Drawing Sheets

(51) Int. Cl.
*F04C 15/00* (2006.01)
*F04C 18/00* (2006.01)
*F04C 11/00* (2006.01)

(58) Field of Classification Search
CPC .. F16J 15/366; F16J 15/16; F16J 15/34; F16J 15/3464
See application file for complete search history.

(56) References Cited

U.S. PATENT DOCUMENTS

| | | | |
|---|---|---|---|
| 3,020,052 A * | 2/1962 | Gits | F16J 15/36 |
| | | | 277/392 |
| 3,165,065 A * | 1/1965 | Stickel | F04C 15/0076 |
| | | | 418/48 |
| 7,131,827 B2 | 11/2006 | Jäger et al. | |
| 2011/0033279 A1 | 2/2011 | Akamatsu et al. | |
| 2013/0115058 A1 | 5/2013 | Hayashimoto et al. | |
| 2022/0362056 A1* | 11/2022 | Algawi | A61M 1/80 |

FOREIGN PATENT DOCUMENTS

| | | |
|---|---|---|
| EP | 934464 A1 | 8/1999 |
| EP | 2295800 A2 | 3/2011 |
| WO | 2021001742 A1 | 1/2021 |

* cited by examiner

SEALING ASSEMBLY FOR A PROGRESSIVE CAVITY PUMP

CROSS-REFERENCE TO RELATED APPLICATIONS

This application claims the benefit of U.S. Provisional Patent Application 63/309,779, filed Feb. 14, 2022, whose disclosure is incorporated herein by reference.

FIELD, BACKGROUND AND SUMMARY

This disclosure relates generally to sealing devices, and specifically to sealing devices for a pump such as a progressive cavity pump.

Progressive cavity pumps may be used during a phacoemulsification procedure performed on an eye of patient, the pumps acting to both provide irrigating fluid to the eye, as well as to aspirate matter removed from the eye. The pumps have a number of advantages, for example being self-priming and being capable of providing large or small rates of flow of the material they are pumping. However, in operation the rotor of a progressive cavity pump travels in a planetary motion within a stator of the pump, i.e., the rotor does not simply rotate around its own axis, it both rotates about its axis and moves in a planetary motion. Consequently, in contrast to the rotor of a pump that only rotates about its own axis, it is more difficult to seal the rotor of a progressive cavity pump.

Examples of the present invention provide a sealing assembly for a progressive cavity pump that is based on an elastic conical diaphragm that effectively forms a seal between the moving and rotating rotor of the pump and the stator of the pump. One opening of the conical diaphragm effectively grips the rotor, the other end of the diaphragm is located to effectively seal to the stator of the pump.

In addition to the sealing assembly preventing leakage of fluid from the pump, the elastic diaphragm acts to reduce variations in pressure due to the oscillatory nature of the fluid flow from a progressive cavity pump.

The present disclosure will be more fully understood from the following detailed description of the examples thereof, taken together with the drawings, in which:

DESCRIPTION OF EXAMPLES

Figure 1:
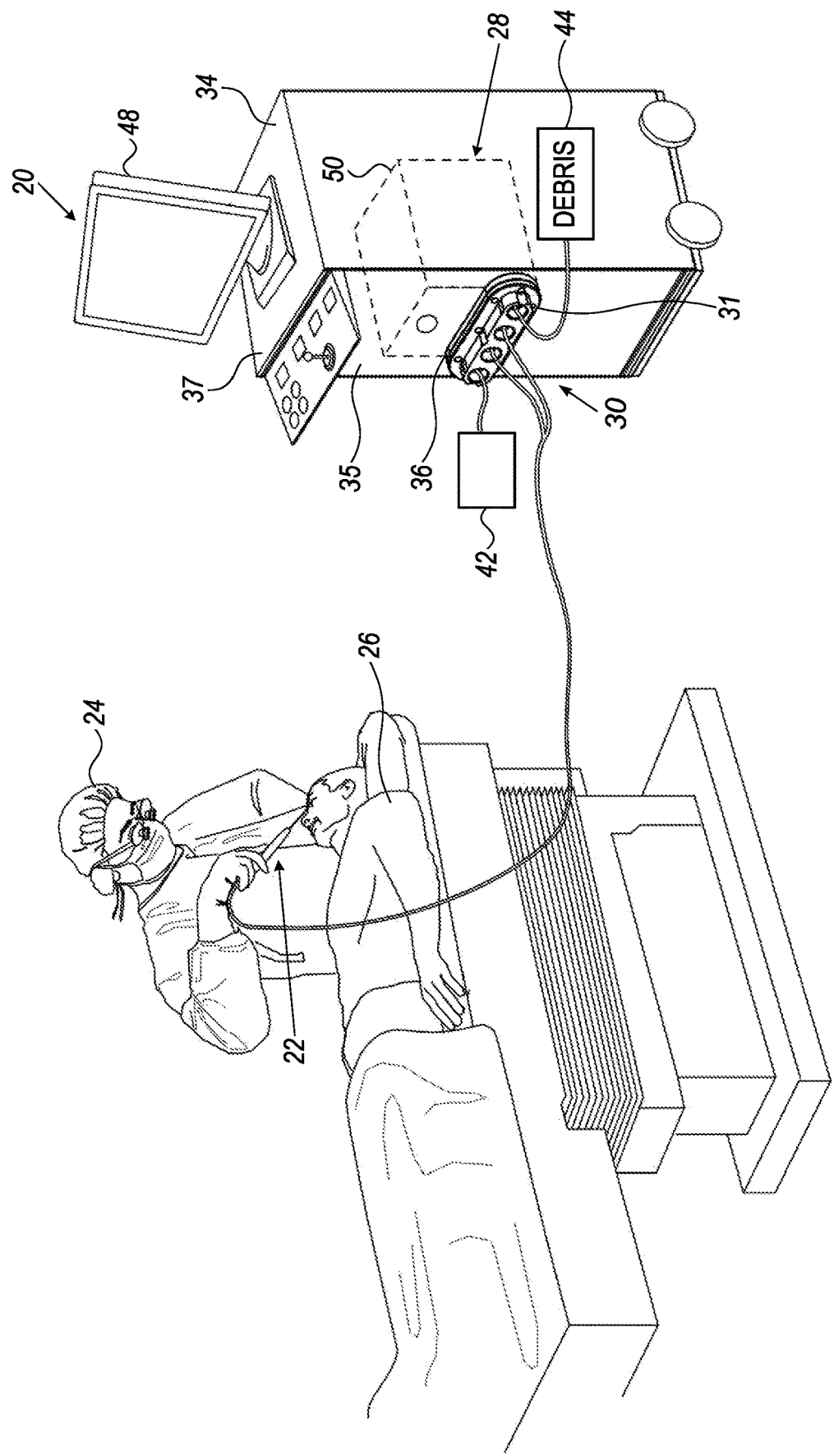
FIG. 1 is a schematic illustration of a phacoemulsification system.

Reference is now made to FIG. 1, which is a schematic illustration of a phacoemulsification system 20. System 20 comprises a phacoemulsification probe 22, which a physician 24 may use to perform a phacoemulsification procedure on an eye of a subject 26. In particular, physician 24 may position the distal tip of probe 22 near or against the lens of the eye. Subsequently, the physician may cause an ultrasonic transducer in the probe to vibrate the distal tip of the probe and to emit ultrasonic waves into the lens via the distal tip, thus causing phacoemulsification of the lens.

System 20 further comprises a fluidics system 28, which is described below. As the phacoemulsification procedure is performed, fluidics system 28 aspirates debris (including pieces of the lens) from the eye while maintaining a flow of an irrigating fluid, such as a balanced salt solution, to the eye so as to maintain the intraocular pressure in the eye.

More specifically, fluidics system 28 comprises a cartridge 30, comprising two progressive cavity pumps 29 (described with reference to FIGS. 2A, 2B, 2C), and a base 50, comprising two motors (not shown). Cartridge 30, and elements of the cartridge, are described below with reference to FIGS. 2A, 2B, and 2C. Prior to the procedure, cartridge 30 is inserted into base 50 such that each pump 29 is mechanically coupled with a different respective motor. Subsequently, one of the pumps, driven by one of the motors, pumps irrigating fluid from a reservoir 42 to the distal end of the probe. The other pump, driven by the other motor, pumps fluid and debris from the eye to a collection container 44.

Typically, base 50 is disposed within, or is an integral part of, a console 34, and cartridge 30 is inserted into the base through a slot 36 in a side panel 35 or top panel 37 of console 34. The cartridge 30 has irrigation and aspiration lines that couple with probe 22 by a connector 31. Ports of the cartridge, for the irrigation and aspiration lines, and for connecting to reservoir 42 and container 44, are described further below with respect to FIG. 2A. Following the procedure, cartridge 30 may be removed from base 50. Typically, cartridge 30 is then disposed of, and another cartridge is used for the next procedure.

In some examples, system 20 further comprises a display 48. System 20 may further comprise a processor and/or other circuitry (not shown), configured to drive the ultrasonic transducer of probe 22, control fluidics system 28, display relevant information on display 48, and/or perform any other relevant function.

Figure 2A:
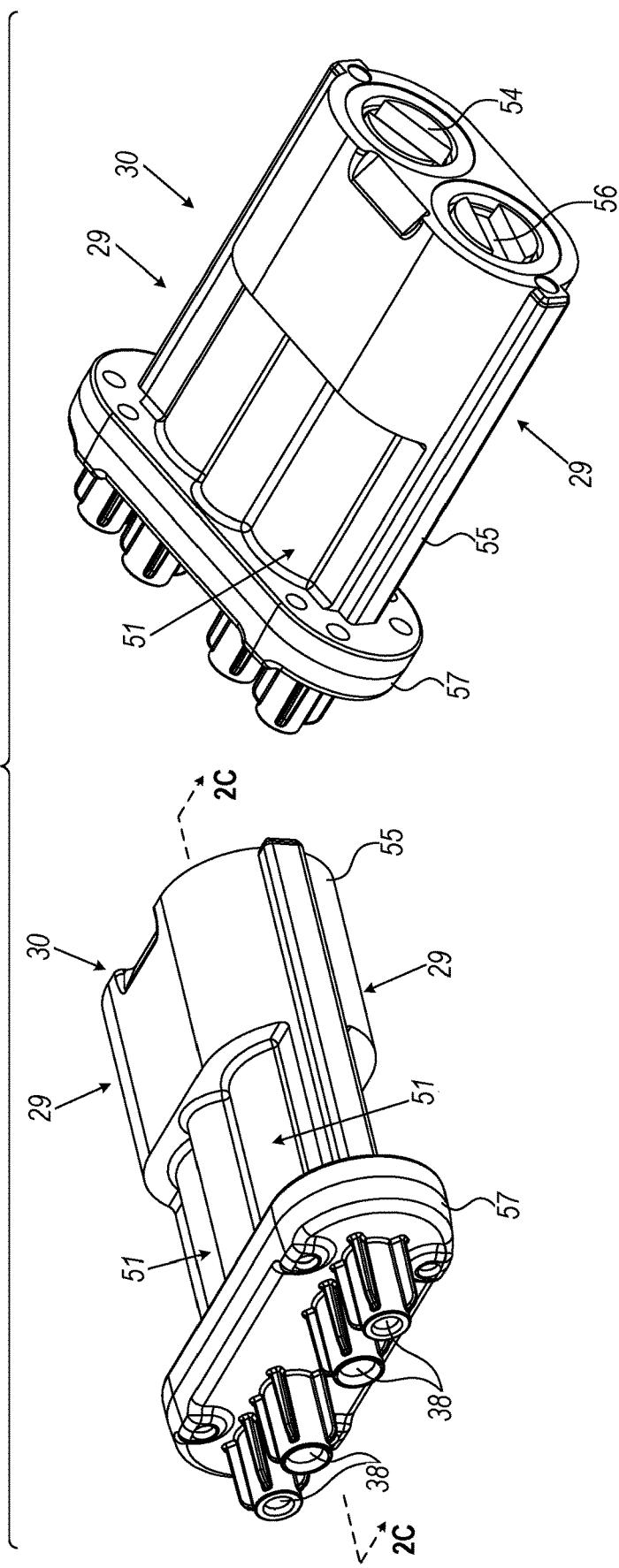
FIGS. 2A, 2B, and 2C are schematic illustrations of a cartridge, having progressive cavity pumps, used in the system of FIG. 1.
Figure 2B:
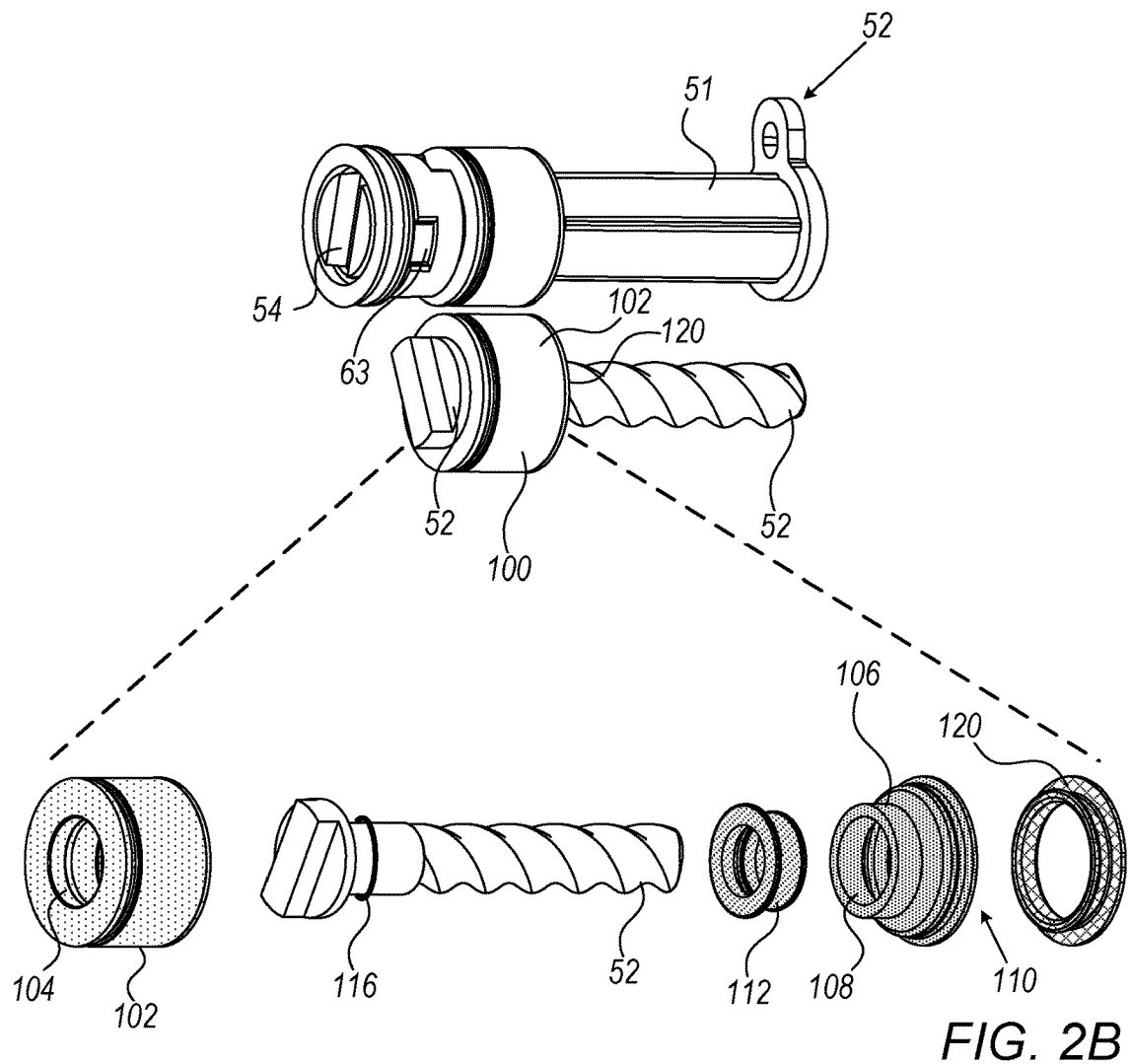
Figure 2C:
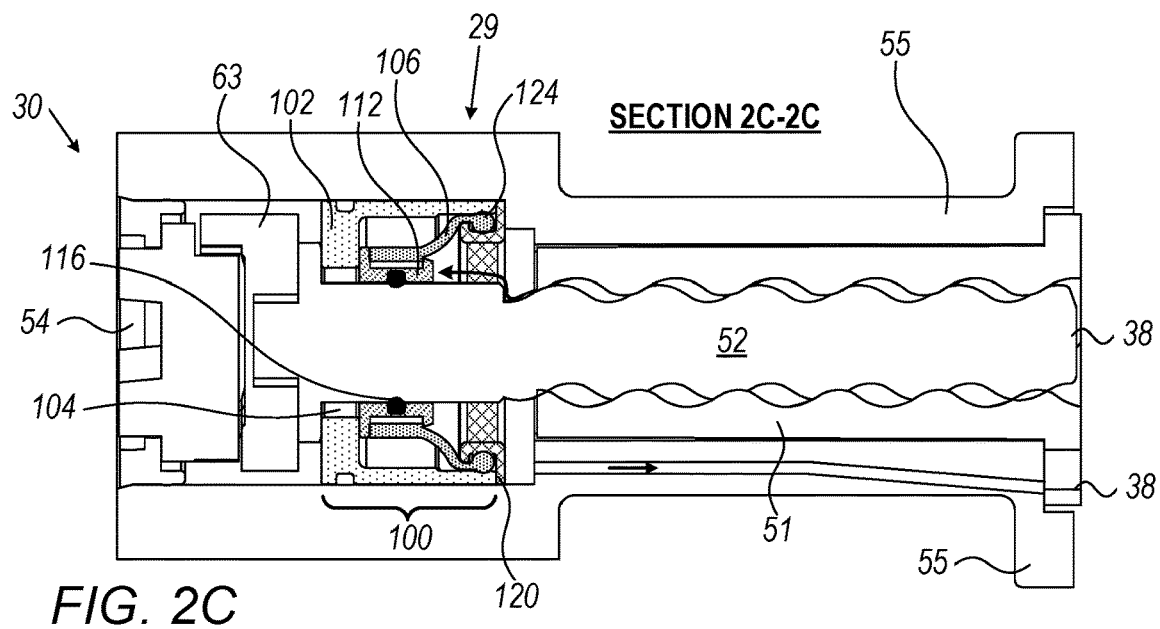

A more detailed description of cartridge 30 is provided with reference to FIG. 2A, which schematically shows cartridge 30 from two different perspectives, and with reference to FIG. 2B and FIG. 2C. FIG. 2B shows internal elements of cartridge 30, with some of the internal elements being shown in a partially exploded form. FIG. 2C is a longitudinal cross section through one of the pumps of the cartridge.

As illustrated in FIG. 2A, cartridge 30 comprises a cartridge housing 55 and a frontal section 57. Housing 55 is shaped to define and retain two stators 51 and the frontal section 57 comprises respective pairs of ports 38 which are in fluidic communication with stators 51. Ports 38 also couple to connector 31. One stator 51 of one pump 29 of the cartridge is illustrated in FIG. 2B (the stator of the other pump is not shown so that the rotor of the other pump is visible). Stators 51 may be metallic or polymeric.

The cartridge further comprises two rotors 52 (FIGS. 2B and 2C) rotatably disposed, respectively, within the stators 51. The cross section in FIG. 2C is shown without frontal section 57 and illustrates one rotor 52 disposed within a stator 51. Rotors 52 may be metallic or polymeric.

As described above with reference to FIG. 1, typically, one pair of ports 38 is connected to reservoir 42 and to the probe 22, while the other pair of ports 38 is connected to the probe 22 and to collection container 44. Thus, rotation of a rotor 52 within a stator 51 of one pump 29 causes irrigation fluid to flow from reservoir 42 to the distal tip of probe 22; and rotation of the other rotor 52 within the other stator 51 of the other pump 29 causes fluid and debris to flow from the eye to collection container 44.

As stated above, pumps 29 are progressive cavity pumps, and the rotors of these pumps, as is known in the art, rotate in a planetary motion. In order to convert the rotary motion of the motors of base 50 to the required planetary motion, examples of the present invention comprise Oldham couplings 63, and the couplings 63 are attached to respective connectors 54. Each connector 54 has a non-circular external section that is typically female. In the illustrated example the external sections of respective connectors 54 comprise troughs 56 (FIG. 2A), and the shafts of the motors of base 50 are configured to connect to troughs 56.

In FIG. 2C arrows schematically illustrate the flow of fluid in one of pumps 29, between the pair of ports 38 of the pump 29. In order to prevent fluid leakage from the pump during the flow, each pump 29 comprises a sealing assembly 100. Each assembly 100 maintains the integrity of the pump by only allowing fluid to transfer between the pair of ports 38 of the pump. Assembly 100 is shown in an assembled state in FIG. 2C and the upper part of FIG. 2B, and elements of assembly 100 are shown in an exploded state in the lower part of FIG. 2B.

Assembly 100 comprises an outer retaining sleeve 102 having an aperture 104 configured to retain rotor 52, while having a diameter that is larger than the diameter of the rotor. Thus, as illustrated in FIG. 2C, there is a gap between the aperture 104 of the outer retaining sleeve 102 and rotor 52. Sleeve 102 encloses an elastic diaphragm 106 that may have a conical shape, the diaphragm 106 terminating at a proximal end of the diaphragm in a first opening 108, and at a distal end of the diaphragm in a second opening 110, larger than the first opening.

First opening 108 of the diaphragm 106 is configured to grip an inner retaining sleeve 112, which in turn retains an elastic O-ring 116. O-ring 116 encircles rotor 52, so that the first opening of the diaphragm 106, using the inner sleeve 112 and the O-ring 116, effectively grips rotor 52.

Second opening 110 of the diaphragm is held in contact with outer retaining sleeve 102 by a ring 120, and the ring 120 is in turn held in contact with an inner surface of housing 55. The ring 120 thus holds the second opening 110 of the diaphragm 106 in proximity to, and substantially fixed with respect to, and in sealing contact with, the stator 51 of pump 29. The contact of second opening 110 of diaphragm 106 with sleeve 102 and ring 120 is enhanced, in an example of the present invention, by a thickening 124 of opening 110. Thickening 124 can be of any shape or thickness necessary to maintain contact with sleeve 102 and ring 120.

As is apparent from inspection of FIG. 2C, in a region between the distal side of diaphragm 106 and a proximal end of stator 51, fluid is present during operation of pump 29. However, the elastic properties of the diaphragm 106 and the O-ring, together with the arrangement of these elements within assembly 100, ensure that no fluid leaks from the assembly.

Furthermore, the space between the proximal side of diaphragm 106 and an inner surface of outer retaining sleeve 102, as well as the larger diameter of aperture 104 compared with the diameter of rotor 52, permit the planetary motion of the rotor 52 that is required during operation of the pump 29.

Progressive cavity pumps, such as pumps 29, operate by moving discrete volumes of fluid, within respective cavities, through the pump. The discrete nature of the flow means that there is inherently pulsation of the flow, so that there is an oscillation of the pressure. In examples of the present invention, the elastic nature of diaphragm 106 acts to dampen the oscillations of the pressure.

It will be appreciated that the examples described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. A sealing assembly for a progressive cavity pump comprising a rotor disposed within a stator, the sealing assembly comprising:
    a retaining sleeve;
    a ring; and
    an elastic diaphragm terminating in a first end of the elastic diaphragm in a first opening, and in a second end of the elastic diaphragm, opposite the first end, in a second opening larger than the first opening, wherein the second opening is held in contact with the retaining sleeve by the ring, and wherein the first opening is configured to grip the rotor of the progressive cavity pump, and wherein the ring is configured to hold the second opening fixed with respect to the stator of the progressive cavity pump.

2. The sealing assembly according to claim 1, further comprising a further sleeve that is configured to be positioned between the first opening of the elastic diaphragm and the rotor.

3. The sealing assembly according to claim 2, further comprising an O-ring, wherein the O-ring is configured to be positioned between the further sleeve and the rotor, and wherein the O-ring is configured to grip the rotor.

4. The sealing assembly according to claim 2, wherein the O-ring is elastomeric.

5. The sealing assembly according to claim 1, wherein the retaining sleeve comprises an aperture having an aperture diameter, and wherein the rotor is located within the aperture and has a rotor diameter smaller than the aperture diameter so as to permit the rotor to move in a planetary motion.

6. The sealing assembly according to claim 1, wherein an inner surface diameter of the retaining sleeve is larger than a diameter of the first opening of the elastic diaphragm, so as to permit the rotor to move in a planetary motion.

7. The sealing assembly according to claim 1, wherein the elastic diaphragm has a conical shape.

8. The sealing assembly according to claim 1, wherein the elastic diaphragm is configured to dampen oscillations of pressure in fluid flowing through the progressive cavity pump.

9. A progressive cavity pump assembly, comprising:
    a cartridge comprising a cartridge housing and a frontal section, wherein the cartridge housing is configured to retain a first stator, a second stator, a first rotor, and a second rotor, wherein the first rotor and the second rotor are disposed within the first stator and the second stator to define a first progressive cavity pump and a second progressive cavity pump of the progressive cavity pump assembly, respectively, and wherein the frontal section comprises a first pair of ports and a second pair of ports that are fluidly coupled with the first stator of the first progressive cavity pump and the second stator of the second progressive cavity pump, respectively, and
    at least one of the first progressive cavity pump and the second progressive cavity pump including a sealing assembly, wherein the sealing assembly, comprising:
    a retaining sleeve;
    a ring; and
    an elastic diaphragm terminating in a first end of the elastic diaphragm in a first opening, and in a second end of the elastic diaphragm, opposite the first end, in a second opening larger than the first opening, wherein the second opening is held in contact with the retaining sleeve by the ring, and wherein the first opening is configured to grip at least one of the first rotor of the first progressive cavity pump and the second rotor of the second progressive cavity pump, and wherein the ring is configured to hold the second opening fixed with respect to at least one of the first stator or the second stator.

10. The progressive cavity pump assembly according to claim 9, further comprising a further sleeve that is configured to be positioned between the first opening of the elastic diaphragm and the at least one of the first rotor and the second rotor.

11. The progressive cavity pump assembly according to claim 10, further comprising an O-ring, wherein the O-ring is configured to be positioned between the further sleeve and the at least one of the first rotor and the second rotor, and wherein the O-ring is configured to grip the at least one of the first rotor and the second rotor.

12. The progressive cavity pump assembly according to claim 10, wherein the O-ring is elastomeric.

13. The progressive cavity pump assembly according to claim 9, wherein the retaining sleeve comprises an aperture having an aperture diameter, and wherein the at least one of the first rotor and the second rotor is located within the aperture and has a rotor diameter smaller than the aperture diameter so as to permit at least one of the first rotor and the second rotor to move in a planetary motion.

14. The progressive cavity pump assembly according to claim 9, wherein an inner surface diameter of the retaining sleeve is larger than a diameter of the first opening of the elastic diaphragm, so as to permit the at least one of the first rotor and the second rotor to move in a planetary motion.

15. The progressive cavity pump assembly according to claim 9, wherein the elastic diaphragm has a conical shape.

16. The progressive cavity pump assembly according to claim 9, wherein the elastic diaphragm is configured to dampen oscillations of pressure in fluid flowing through the progressive cavity pump assembly.

* * * * *